United States Patent [19]

Carlon et al.

[11] Patent Number: 4,568,190

[45] Date of Patent: Feb. 4, 1986

[54] ELECTROOPTICAL SYSTEM AND TECHNIQUE FOR DIRECT QUANTITATIVE MEASUREMENT OF THE MASS CONCENTRATION OF MONODISPERSE AEROSOLS

[75] Inventors: Hugh R. Carlon, Edgewood; David V. Kimball, Aberdeen; Robert J. Wright, Joppa, all of Md.

[73] Assignee: The United States of America as represented by the Secretary of the Army, Washington, D.C.

[21] Appl. No.: 661,528

[22] Filed: Oct. 15, 1984

Related U.S. Application Data

[63] Continuation of Ser. No. 557,468, Feb. 6, 1984, which is a continuation of Ser. No. 272,588, Jun. 18, 1981.

[51] Int. Cl.[4] ............................................. G01N 21/00
[52] U.S. Cl. .................................... 356/439; 356/440
[58] Field of Search ............... 356/335, 440, 336, 337, 356/338, 432, 437, 438, 439

[56] References Cited

U.S. PATENT DOCUMENTS 3,609,043  9/1971  Simmons et al. .................... 356/335
3,740,149  6/1973  Whetten .............................. 356/335

OTHER PUBLICATIONS

Trausk et al., "Light Transmission Instrument for Particle Size Analysis of Colloidal Dispersion", *Power Technology*, vol. 27, No. 2 (Nov./Dec. 1980), pp. 215-218.
Dobbins et al., "Particle Size Measurements Based on Use of Mean Scattering Cross Sections", *Journal of the Optical Society of America*, vol. 56, No. 10 (Oct. 1966), pp. 1351-1354.
Strobel, H. A., *Chemical Instrumentation*, ©1960, Addison-Wesley Publishing Co., p. 222.

"Turbidimeter", Turbidimetry and Nephelometry, *Van Nostrand's Scientific Encyclopedia*, pp. 1900-1901.

*Primary Examiner*—R. A. Rosenberger
*Attorney, Agent, or Firm*—Anthony T. Lane; Robert P. Gibson; Michael C. Sachs

[57] ABSTRACT

An electrooptical system and technique for direct quantitative measurement of the mass concentration of monodisperse aerosols by means of filling an enclosed chamber with a cloud or a sequence of separate clouds of essentially transparent and spherical, aerosolized particles or droplets of known density and known or selectively controlled particle size. While within the confines of the chamber the cloud, or each of the sequence of clouds, of aerosolized particles is maintained in a homogeneous condition and irradiated with a beam of high-intensity and constant wavelength irradiation selected to possess a wavelength to particle size ratio wherein attenuation of the irradiation will be almost exclusively, if not nearly entirely, attributable to optical scattering. The mass concentration of the cloud, or each of the sequence of clouds, of aerosolized particles is directly and quantitatively measured, or monitored, as a direct function of the measured magnitude, or intensity, of the attenuated beam of irradiation transmitted through the cloud. The results provide a reliably accurate measurement to within a minimal margin of error of ±10% or less.

The system and technique provide a relatively quick and inexpensive means and procedure for calibrating the accuracy, or efficiency of various types of aerosol sampling devices and equipment by affording a chamber from which a known volume of the cloud of monodisperse aerosolized particles may be aspirated into the sampling device or equipment while electrooptically measured. The measured results attained by use of the sampling device may then be compared for accuracy purposes with the electrooptically measured results.

12 Claims, 2 Drawing Figures

ELECTROOPTICAL SYSTEM AND TECHNIQUE FOR DIRECT QUANTITATIVE MEASUREMENT OF THE MASS CONCENTRATION OF MONODISPERSE AEROSOLS

GOVERNMENTAL INTEREST

The invention described herein may be manufactured, used and licensed by or for the Government for governmental purposes without the payment to us of any royalty thereon.

BACKGROUND OF THE INVENTION

1. Field of the Invention

The present invention relates generally to electrooptical measurement of aerosols as a means for determining the mass concentration of the particles or droplets contained therein, and more particularly, pertains to an electrooptical system and technique for direct quantitative measurement of the mass concentration of the constituent particles or droplets of a given monodisperse aerosolized medium.

2. Description of the Prior Art

Heretofore, various techniques have been employed in endeavors to accurately and precisely determine various characteristics and properties of aerosolized particles. Many of these prior techniques utilize devices and equipment necessitating the transfer or extraction of a representative sample of the aerosol which is to be analyzed, or measured, in order to determine the properties and characteristics of the particle or droplet constituents of the aerosol under investigation. Obviously, the ability to obtain a truly representative sample is dependent to a great extent upon the manner in which the sample is obtained. No less importantly, the sampling technique and equipment, or device, must be designed in such manner that it provides the capability of extracting a truly representative sample of the aerosol to be subjected to study or at least be capable of providing a sample which is representative within a known margin of error.

One commonly followed approach to the problem of determining the accuracy, or efficiency, of the sampling technique, or device, is to test the sampling capability thereof by the expedient of comparing its sampling results against the sampling results obtained with a standard sampler tube which has been precalibrated, or pretested, for sampling accuracy and, hence, possesses a known efficiency with respect to the aerosol properties and characteristics for the procedures used for such precalibration. If the precalibration was obtained by comparison with another precalibrated standard sampler, as discussed above, which in turn was similarly precalibrated, etc., the degree of the accuracy of the standardization technique tends to become increasingly suspect as each new generation of standard samplers evolves. Alternatively, a somewhat better approach for determining the accuracy, or efficiency, of the sampling device is to utilize it in conjunction with a test, or standard, aerosol possessing known properties or characteristics, such as, for example, known composition, mass, or number concentration, and particle size distribution. In accordance with this latter approach, a quantity, or aliquot portion, of the test aerosol ordinarily is aspirated at a known flow rate for a known period of time into the aerosol sampler from a chamber containing the test aerosol. Thereafter, the mass of the aerosol collected within the sampler is gravimetrically determined in conventional manner. The particle mass of the aerosol collected by the sampler is then compared directly with the known, mass concentration of the test aerosol contained within the aerosol test chamber to thereby determine the accuracy, or efficiency, of the sampler. However, while this latter approach provides a more reliably accurate method of original standardization, or precalibration, of an aerosol sampler, it is dependent upon a comparative assessment of the results obtained by the sampler and the results ordinarily obtained by difficult and extremely complex Mie-theory calculations, aerosol model-studies, and the like from which the needed information with respect to particle mass, mass concentration, particle size-distribution and the like are derived. Obviously, such calculations and studies are extremely costly and time-consuming. Hence, the art of accurate, aerosol sampling is in great need of a technique and apparatus capable of providing extremely accurate monitoring of the physical characteristics of aerosolized particles and of providing a highly accurate means of determining the sampling efficiencies of aerosol samplers generally or for standardization and precalibration purposes.

Since the true accuracy, or efficiency, of the sampler is based upon the accuracy of the known values attributed to the test, or standard, aerosol from which the sample was taken, it is, of course, exceedingly important that such properties as, for example, the particle size, mass concentration and the like, of the test aerosol be monitored as closely as possible for knowledge of any changing conditions. Such close monitoring, however, is very difficult and presents an extremely complicated and challenging task, since the establishment and maintenance of a test aerosol possessing a high degree of constancy in its properties and characteristics is an extremely complex problem. Customarily and according to past practices, the test aerosol is periodically sampled to ascertain if, and in what manner, the properties and characteristics thereof have undergone change as a result of an elapse of time during which particle agglomeration and settling commonly can and do tend to occur. This problem is frequently further aggravated by the fact that the sampling of the test aerosol involves the withdrawal of a representative sample which in and of itself constitutes a source of disturbance and diminishment of the chamber-contained, test aerosol. Moreover, during the time required to complete an accurate analysis of each withdrawn sample of test aerosol, which ordinarily requires at least several minutes duration, the properties and characteristics of the aerosol within the test chamber remain subject to continued or further alteration. In view of these and other problems associated with past aerosol sampling procedures, a technique for more precisely and more rapidly monitoring the properties and characteristics of a test aerosol of the foregoing type is a matter of significant importance and concern.

SUMMARY OF THE INVENTION

In accordance with one broad aspect, the present invention pertains to a unique electrooptical system and technique for direct quantitative measurement of the mass concentration characteristics of aerosols composed of transparent, or essentially transparent, spherical particles. The system and technique embody the innovative concept of generating from a selected medium of known density a cloud of monodisperse aerosol particles, or droplets, of known, or selectively controlled, particle size and of irradiating the particles with a high-intensity beam of light selected to possess a wavelength wherein attenuation of the high-intensity irradiation will be almost exclusively, if not nearly entirely, attributable to optical, or light, scattering effects, and wherein only minimal, or nonappreciable, attenuation of the high-intensity irradiation will be attributable to light, or optical, absorption effects. Otherwise stated, the particle size of the aerosolized, monodisperse particles and the wavelength of the high-intensity irradiation are selectively correlated to achieve light-attenuation, or light extinction, effects resulting essentially entirely from geometric optical scattering, such as occurs when the particle sizes, or diameters, of the aerosolized particles are much larger than the wavelength of the high-intensity irradiation used for observational purposes. To this end a source of high-intensity irradiation having a wavelength no more than one-fourth of the particle size of the aerosolized particles is employed for observational purposes. The high-intensity irradiation is beamed along an optical path, or optical axis, traversing a cloud of transparent, or essentially transparent, monodisperse particles confined and maintained in a uniformly dispersed condition within a chamber of known, or determinable, dimensional size. The magnitude, or intensity, of the beam transmitted through the cloud is measured, or monitored, by a suitable detector stationed on the opposite side of the chamber in registered optical alignment with the optical axis of the beam of irradiation, and the intensity, or magnitude, of the transmitted irradiation provides a quick and convenient system and technique for direct quantitative measurement of the mass concentration of the aerosolized particles within a margin of accuracy of about ±10 percent.

In accordance with another aspect of the invention, a series of separate aerosol clouds of monodisperse particles of incrementally varying particle size and covering a selected particle size range is generated and electro-optically measured in the above-described manner to quantitatively determine the mass concentration for each of the series of separate clouds. Additionally, an aspirated aliquot portion of each separate aerosol cloud is aspirated from the chamber into a candidate aerosol sampler and the mass concentration gravimetrically determined. Based upon the relative or comparative results of the electrooptical and gravimetric measurements, the efficiency, and hence accuracy, of the aerosol sampler is thereby established for a given range of particle sizes. Thus, a quick, accurate and inexpensive system and technique is provided for standardizing and calibrating the sampling efficiency of various types of aerosol samplers such as may be used in conjunction with diverse kinds of aerosol sampling equipment and devices.

In keeping with the above, it is accordingly an objective of the present invention to provide an electrooptical system and process, or technique, for quantitatively measuring, or monitoring, the mass concentration characteristics of aerosolized particles.

Another objective is to provide a system and process which in addition to being capable of accomplishing the foregoing objective is also capable of providing direct and continuous measuring, or monitoring of the mass concentration characteristics of the aerosolized particles.

Another objective of the present invention resides in the provision of an electrooptical system and technique for quickly, inexpensively and accurately calibrating the mass concentration sampling efficiency of various aerosol sampling devices and equipment.

A further objective of the present invention is the provision of an electrooptical technique, or process, for directly and quantitatively measuring the mass concentration characteristics of aerosolized particles, and wherein the process is characterized by comprising the following steps:

selecting an aerosol particle size and a wavelength of high-intensity irradiation with which to irradiate the aerosol particles, the selection being correlated to restrict attenuation of the irradiation by the particles essentially exclusively to attenuation resulting from geometric optical scattering;

filling an essentially enclosed chamber with an aerosolized cloud of monodisperse particles having the selected particle size;

projecting a constant wavelength beam of high-intensity irradiation having the selected wavelength through the aerosolized cloud;

monitoring the magnitude of the beam of high-intensity irradiation traversing through the aerosolized cloud and directly and quantitatively measuring the mass concentration of the particles therein as a function of the monitored magnitude of the attenuated beam.

A still further objective of the present invention is the provision of an electrooptical system for directly and quantitatively measuring the mass concentration characteristics of aerosolized particles and wherein the system is characterized by comprising:

means defining a chamber within which to confine a cloud of aerosolized particles;

means for emitting a beam of high-intensity irradiation of selected constant wavelength along a linear optical path traversing the confines of the chamber;

means for filling the chamber with a cloud of monodisperse aerosolized particles of selected particle size;

the selected wavelength of the high-intensity irradiation and the selected particle size of the cloud of aerosolized particles being selectively correlated to restrict attenuation of the beam of high-intensity irradiation essentially exclusively to attenuation resulting from geometric optical scattering; and light-sensor means arranged in optical registry with the optical path of the beam of high-intensity irradiation and interspaced across the chamber from the emitting means for sensing the magnitude of the attenuated beam of high-intensity irradiation traversing the cloud of aerosolized particles and for quantitatively measuring the mass concentration of the cloud of aerosolized particles as a direct function of the sensed magnitude of the attenuated beam.

A still further objective of the present invention is the provision of a technique and system respectively embodying the characteristics of the last-mentioned two objectives and which provide a quick, inexpensive, highly accurate technique and system for use in measuring or calibrating the accuracy, or efficiency, of various sampling devices and equipment used to measure or monitor the mass concentration of aerosolized particulates in the atmosphere or other environs.

These and other additional objectives, features and advantages of the present invention will become readily apparent to those only ordinarily skilled in the art from the following detailed description taken in conjunction with the accompanying sheets of drawings.

DETAILED DESCRIPTION OF THE INVENTION

Figure 1:
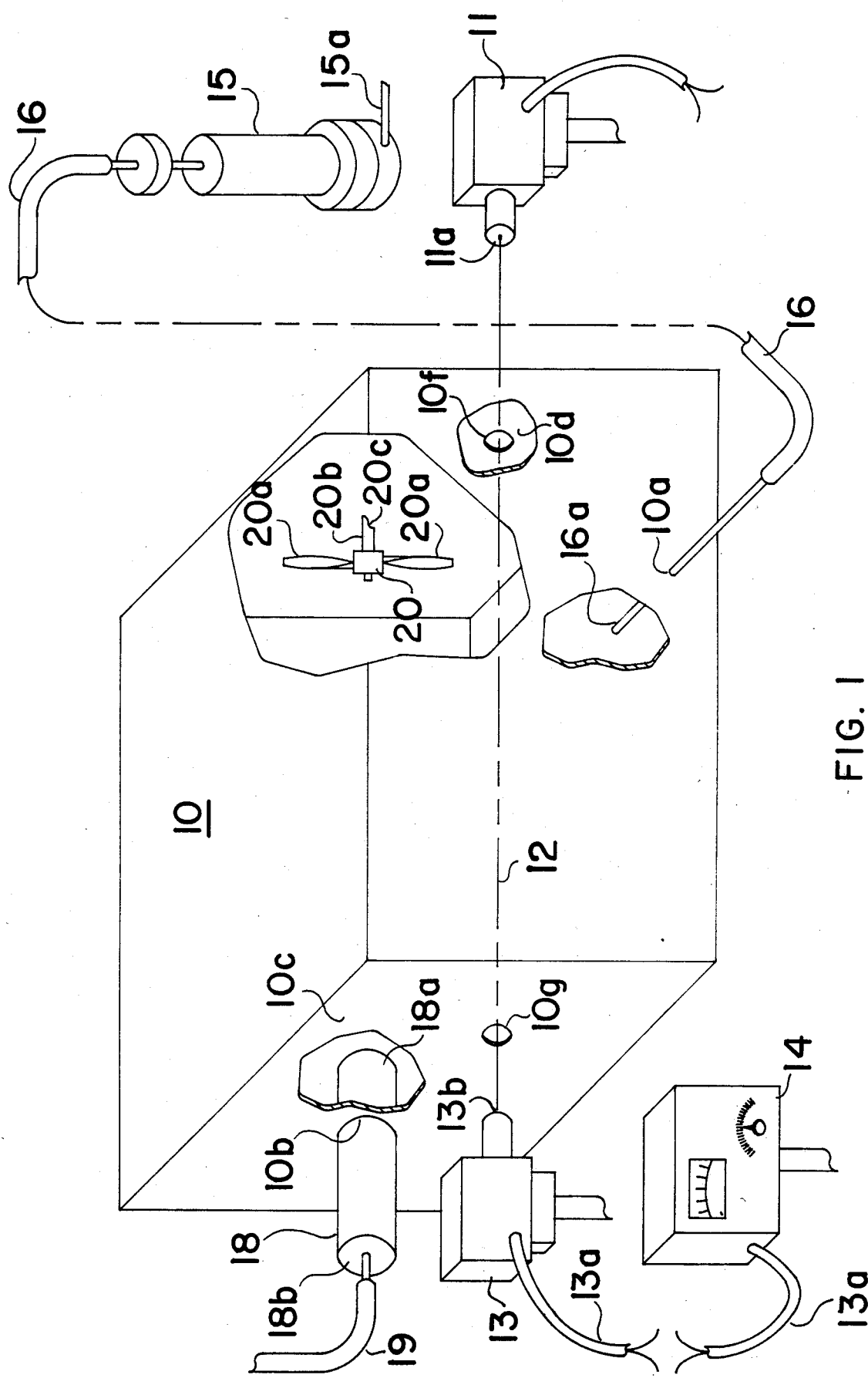
FIG. 1 schematically depicts a partially fragmentary, perspective view of an aerosol test chamber and associated equipment for establishing, maintaining and directly monitoring the properties and characteristics of a test aerosol in accordance with the innovative techniques of the present invention.

1. Theoretical Basis of Invention.

Based upon experimental and developmental efforts leading to the present invention, it was determined that in conducting optical transmission measurements of aerosols composed of essentially spherical and transparent aerosol particles having particle sizes or diameters on the order of at least about four times larger than the wavelength of the high-intensity, light irradiation employed for optical transmission measurements, the extinction coefficient, within a degree of accuracy of at least ±10 percent, could be considered to be a constant divided by particle diameter regardless of the specific wavelength of high-intensity, light irradiation employed. This determination arose from the observation that particle size to wavelength ratios of this order result in the establishment of the so-called "geometric optical scattering regime" wherein the index-of-refraction component of the aerosolized particles is essentially entirely attributable to optical scattering with no appreciable absorption occurring. Thus, under these conditions optical calculations can be made using the well-known Mie theory, and the Beer-Lambert Law to substantiate the capability of the present invention to effectively measure and monitor to a high degree of accuracy the mass concentration characteristics of aerosols composed of transparent aerosolized particles within the geometric optical scattering regime. For example, it has been determined that in the geometric optical scattering regime, the extinction coefficient for transparent, or essentially transparent, spherical particles may be calculated within a negligible allowable error factor of ±10% by use of Mie-theory calculations derived from the following Equation 1:

$$\alpha_\lambda = \frac{3(Q)_\lambda}{2D\mu \cdot \rho} \quad \text{Equation 1.}$$

wherein:

$\alpha_\lambda$ is the mass extinction coefficient of the spherical particles at the subscript wavelength (m²/gm);

$\lambda$ is the wavelength of light used for observation (μm);

$\rho$ is the particle density (gm/cm³);

$(Q)_\lambda$ is the cross-section efficiency factor at the subscript wavelength;

$D\mu$ is the effective (mean) diameter of the aerosol particles (μm).

Moreover, it has been determined that the cross-section, efficiency factor (Q) is very nearly constant and equal to 2.0 for transparent and essentially spherical aerosol particles, such as, for example, liquid aerosol droplets or the like in the geometric scattering regime. Therefore, by substitution of the constant value of 2.0 for (Q) in the above Equation 1 the equation may be simplified to read, as follows:

$$\alpha_\lambda \simeq \frac{3}{D\mu \cdot \rho} \quad \text{Equation 2.}$$

Further, since the mass extinction coefficient is also used in the well-known Beer-Lambert equation, as follows:

$$ln(1/T_\lambda) = \alpha_\lambda C L \quad \text{Equation 3.}$$

wherein:

$T_\lambda$ is the fractional transmittance at the subscript wavelength (unitless);

$\alpha_\lambda$ is again the mass extinction coefficient at the subscript wavelength as defined above (m²/gm);

C is the aerosol mass concentration (gm/m³); and

L is the optical pathlength through the aerosolized liquid being investigated (m);

it is possible by substitution from Equation 2 to eliminate the extinction coefficient in Equation 3. By so doing Equation 3 may be alternatively expressed in terms of mass concentration (C), particle diameter ($D\mu$), particle density ($\rho$), optical pathlength (L) and fractional transmittance ($T_\lambda$), as follows:

$$C \simeq \frac{D\mu \cdot \rho}{3L} ln(1/T_\lambda) \quad \text{Equation 4.}$$

Thus, by derivation of the foregoing concepts it has been determined that with transparent, or essentially transparent, spherical, monodisperse particles or droplets of a liquid of known or readily determinable density the mass concentration may be directly measured, or monitored, as a direct function of the measured fractional transmittance obtained in response to excitation of the particles by a source of high-intensity irradiation of a known wavelength; provided that the particle size of the monodisperse particles is in the geometric scattering regime with respect to the wavelength of the monitoring irradiation, or light. In accordance with the foregoing theoretical determinations and observations, one preferred system and technique embodying the concepts of the present invention are hereinafter described in more specific detail.

2. Preferred Structural Embodiment.

The overall general organizational arrangement and operational interrelationship of the electrooptical system of the present invention are schematically depicted in FIG. 1. As illustrated, means in the form of an aerosol test chamber 10 defines an essentially enclosed chamber within which to confine a cloud of aerosolized particles (not shown). The aerosol test chamber 10, preferably defines a rectangular configuration, and provides a chamber of known internal volumetric capacity within which to maintain and confine a constant volume, or cloud, of aerosolized particles. In operative association with the chamber 10 there is means, such as a transmissiometer embodying an irradiation emitter 11 for emitting a high-intensity, or high-energy, beam of irradiation, such as a high-intensity light beam and light-sensor means 13. As shown, the irradiation emitter 11 is disposed adjacent to one upright, exterior side of the chamber 10 and has a light-emitting portion 11a for emitting and transmitting a beam of high-intensity irradiation, or light, along a linear optical path, or optical axis 12, extending transversely across the interior of the chamber. The light-sensor means 13 is in the form of a detector having a radiation or light-detecting face 13b disposed in optical registry with the optical path, or axis 12, and is stationed adjacent to an opposite, upright, exterior side of the chamber 10. The light sensor 13 is thus interspaced across the chamber 10 from the irradiation emitter 11 and is provided with an output meter 14, electrically connected by wiring 13a to the light sensor 13, for measuring, or monitoring, the magnitude of the output signal emitted by the light sensor in response to excitation induced by the interception of high-intensity light radiations transmitted through the chamber 10 from the irradiation emitter 11.

In accordance with a significant innovative feature of the present invention, means for generating aerosolized, liquid particles, or droplets, of test aerosol are also provided by an aerosol generator 15 specifically designed to possess the capability of generating a fog of aerosolized liquid particles, or droplets, composed of exceedingly uniform, single size, or "monosize" particles throughout a selectively variable range of monosize particle sizes. The aerosol generator 15 includes a liquid feed line 15a through which to accommodate from a suitable liquid reservoir (not shown) a controlled supply of liquid which is to be aerosolized by the generator. Monosize liquid particles produced by the generator 15 are forcibly dispelled through a discharge outlet into a conduit 16 leading to the chamber 10 and having a discharge end 16a projecting through a chamber, wall port, as at 10a, into the interior confines of the chamber.

One, among other, means for accommodating efficiency testing of aerosol samplers is provided by an access opening 10b extending through chamber sidewall 10c and through which to insert for efficiency calibration purposes a conventional test-candidate, filter-containing, aerosol sampler 18 with its inlet end 18a fully disposed within the interior of the chamber to permit direct and unrestricted communication thereof with test aerosol within the test chamber 10. The opposite outlet end 18b of the sampler 18 is conventionally adapted to be attached to a suitable aspirating device, such as a vacuum pump or the like (not shown), by means of discharge conduit 19. For purposes of ensuring aerosol homogeneity during testing or sampling, means are provided for continuously, thoroughly and uniformly stirring and intermixing the aerosol particles, or droplets, within the confines of the test chamber 10. Such means is schematically depicted in one preferable form, among others, as a rotary fan 20 having fan blades 20a disposed interiorly of the chamber and mounted upon a rotary driving shaft 20b extending axially through a wall port, as at 20c, in the chamber sidewall 10d and adapted to be continuously and uniformly driven during testing and sampling operations by a suitable drive motor, not shown.

In more detailed respects, the test chamber 10, merely by way of preferential design and enhanced observational capability of the interior confines, is fabricated from transparent glass or plastic material and is suitably of rectangular configuration. Oppositely facing chamber sidewalls 10c and 10d are respectively provided with a transverse, pinhole-size aperture, or optical window, such as at 10f and 10g. As shown, windows 10f and 10g are respectively deployed in coaxial alignment with the optical axis 12 and, being openings, avoid spectral interference with respect to the passage of the light beam transmitted along the optical axis between the irradiation emitter 11 and the light sensor or detector 13. Although not shown, the employment of suitable means for providing pressure equalization between the interior and exterior environs of the chamber 10 is preferable to obviate the undesirable potential possibility of escape of any appreciable quantity of aerosol particles from the chamber, by way of the windows 10f and 10g, just described, or other possible escape routes.

Although, for purposes of clarity of illustration, the irradiation emitter 11 and the detector 13 are schematically depicted as being removed somewhat axially outward from the chamber sidewalls 10d and 10c, respectively, it is to be understood that during operational use, the transmissiometer and detector are positioned in close juxtaposition with the sidewall windows 10f and 10g, respectively, to preclude potential spectral aberrations or disturbances such as might result from ambient external radiation sources in the vicinity of the chamber 10 during operational use of the equipment for aerosol testing and monitoring purposes. More specifically, during operational use the irradiation emitter 11 and the detector 13 are deployed with their respective light-emitting and light-detecting faces 11a and 13b disposed in close juxtaposition with the windows 10d and 10g and in mutually-facing, coaxial alignment with each other along the optical axis 12.

A preferred form of liquid aerosol generator 15 for carrying out the practice of the present invention is one which is capable of generating a monodisperse liquid aerosol in a relatively large quantity and at a relative rapid rate in order to assure filling of the test chamber 10 with a uniform and monodisperse aerosol which can be more readily maintained. Additionally, the aerosol generator 15 should preferably be capable of accommodating precisely adjustable particle size selectivity over a relatively wide range of discrete particle sizes; especially in the geometric particle size regime wherein the particles are at least four times, and more preferably, at least five times larger than the wavelength of the light beam emitted by the irradiation emitter 11. One such liquid aerosol generator, among others, which is particularly suitable for utilization in the practice of the present invention is a "spinning-disk" type of generator. One, among other, commercially available spinning disk generators is marketed by Environmental Research Corporation of St. Paul, Minn., under its model number designation Model No. 8320. It has been determined that a liquid aerosol generator of the last-mentioned type is capable of generating an extremely uniform, monodisperse liquid aerosol at selectively controllably particle sizes throughout a particle size range of from about 5 to about 50 micrometers in diameter and in concentrations of 0.1–1.0 gram/cubic meter. Selective control of the particle size, or droplet size, disseminated by the generator is determined by the diameter and angular velocity of the disc, as well as by the rate of flow of the liquid being fed to and impinging upon the disc during rotation and, to a lesser extent, by other conditions including temperature. Verification of the generated droplet size may be readily determined by the conventional technique of microscopic examination of representative droplets deposited upon glass viewing slides.

In accordance with one, among other, highly advantageous aspects of the present invention, is the aspect of the versatile adaptability of the invention with respect to the particular source of high-intensity irradiation which may be utilized. For example, the invention is not restricted to a specific wavelength of light transmitted by the irradiation emitter 11, since it has been discovered that excellent results can be achieved utilizing most any constant wavelength of high-intensity irradiation; provided, that the relationship of the wavelength to the particle size of the aerosol being measured or monitored results in the establishment of an optical attenuation which is essentially entirely attributable to geometric optical scattering. In other words, the particular wavelength of transmitted light is not critical so long as the particle size of the spherical, transparent particles, or droplets, is much larger than the wavelength of the high-intensity irradiation emitted from the irradiation emitter. More specifically, in this regard, it has been discovered that the utilization of particle size to wavelength ratios of at least about four or more provide extremely accurate optical measurements for transparent or essentially transparent monodisperse aerosol particles, or droplets, Hence, the invention affords a considerable degree of flexibility with respect to the selection of the particular transmissiometer desired to be employed in the practice of the invention. Accordingly, for descriptive purposes only, the irradiation emitter 11 may optionally be a helium-neon laser source providing an emission spectra of visible light having a wavelength of 0.63 micrometers at a power output of 0.5 milliwatts. One such commercially available laser source is marketed by Spectra-Physics of Mountain View, Calif. 94042, under designated Model No. 155.

The detector 13, as will be readily understood by one ordinarily skilled in the art, is merely a power meter capable of measuring the intensity, or magnitude, of the light beam transmitted through the aerosol test chamber 10 from the irradiation emitter 11, and accordingly is selected to be compatible with the optionally selected type of irradiation emitter with which it is to be operationally utilized in the practice of the invention. A highly suitable detector unit for use with the helium-neon laser specifically described above is marketed by Metrologic Instruments, Inc., of Bellmawr, N.J. 08031, under the trade name, Laser Power Meter, Model 45-540, and provides measurement capabilities in four power ranges respectively of 0–20 microwatts, 0–200 microwatts, 0–2 milliwatts and 0–200 milliwatts.

3. Mode of Operation.

The operational technique of the present invention, while undoubtedly apparent to those skilled in the art from the foregoing discussion, will be briefly described hereinafter. Initially, an irradiation emitter such as the emitter 11 is selected to provide a source of high-intensity irradiation having a constant wavelength which will be at least four times smaller than the aerosol particle size, or sizes, desired to be electrooptically investigated. Similarly, an aerosol generator such as, for example, the generator 15, is selected which has a capability of quickly generating a relatively high volume of monodisperse liquid particles, or droplets, having the particle size, or particle sizes, desired to be investigated. Following such selection and installation of these and the other system components in the manner previously described, a liquid of known properties and density is fed to the aerosol generator 15 and the generator is adjusted, as necessary, to operationally generate liquid particles, or droplets, of the selectively predetermined particle size desired for investigative purposes. In the case of a spinning-disc type of generator such adjustment is conveniently accomplished by adjustment of the rotational velocity and/or angular attitude of the disc.

Following appropriate particle size adjustment of the aerosol generator, the generated, monodisperse, liquid, aerosol particles are fed from the aerosol generator into the chamber 10 wherein the particles are uniformly and homogeneously distributed throughout the chamber by the rotating blades of the fan 20. After the chamber has been uniformly filled with a cloud of the monodisperse particles such filled and uniform condition is maintained by continued operation of the aerosol generator 15 and the fan 20 and with excess overflow of generated aerosol being obviated, where necessary, by means of a suitable chamber exhaust port or other conventional valving means, or the like, (not shown).

Following attainment of complete chamber filling and equilibrium conditions of the aerosolized cloud within the chamber 10, a measurement of the magnitude of the high-intensity beam of irradiation passing through the cloud from the irradiation emitter is obtained from the light-sensor, output meter 14. Preferably, by suitable precalibration of the output meter, the mass concentration of the cloud of aerosolized, monodisperse particles may be measured directly by the output meter 14, since the mass concentration of the cloud of aerosolized particles is a direct, log relationship of first order magnitude to the intensity of the attenuated irradiation detected by the detector 13 and measured by the output meter. It is also to be understood that prior to regular operational use, the output meter 14 is initially test-calibrated so as to be in accord with mass concentration values derived in accordance with Mie theory and Beer-Lambert law calculations previously described.

Attainment and maintenance of stabilized, uniform conditions of the cloud of aerosolized particles within the chamber 10 is, of course, an essential requisite to accurate quantitative measurements of the cloud properties. Such stability and uniformity is readily and easily determinable in accordance with the practice of the present invention. By maintaining a continuous monitoring of the measurement readings provided by the output meter 14, which is highly sensitive to changes in particle concentration, distribution and the like, changes, if any, occurring in the properties of the aerosol cloud within the chamber will be quickly and easily detected.

In accordance with a further aspect of the above-described technique, the present invention provides a reliably accurate process for quickly and inexpensively measuring or calibrating the sampling accuracy of various other types of aerosol sampling devices and equipment. In keeping with this further aspect of the invention, a measured volume of the aerosolized cloud, while in a stabilized condition as indicated by the output meter 14, is aspirated into the candidate aerosol sampling device. The weight, or mass, per unit of collected volume of the monodisperse aerosol particles collected by the sampling device is then determined and compared with the electrooptically determined mass per unit of volume of monodisperse, aerosol particles contained within the chamber 10. The comparative results provide a relative accuracy, or efficiency, rating for the sampling device with respect to the particular size of the monodisperse particles within the chamber. Repetition of the foregoing procedure with respect to an incremental range of monodisperse particle sizes may then be conducted to establish the sampling accuracy of the sampling device with respect to a range of particle sizes.

Figure 2:
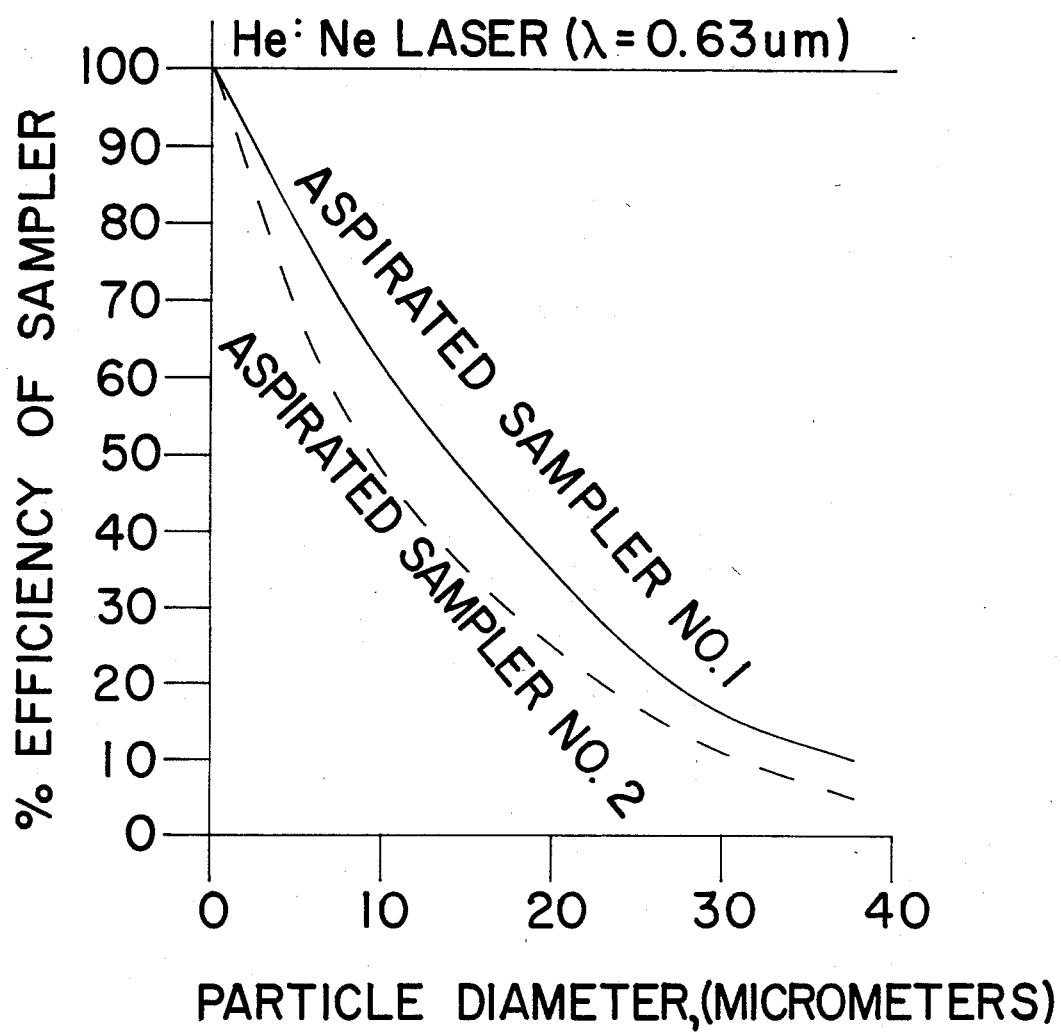
FIG. 2 is a graphic representation comparatively depicting, for spherical aerosol particle diameters ranging up to about 40 micrometers in size, the relative aerosol sampling efficiencies achieved by utilization of the innovative technique and system of the present invention as compared with two conventional aerosol sampling devices utilized in accordance with conventional sampling procedures.

Exemplary results of mass concentration measurements obtained through the use of the above-described system and technique are graphically depicted in FIG. 2. As shown, the aerosol mass concentration sampling efficiencies of two representative aerosol samplers, indicated as Aspirated Sampler No. 1 and Aspirated Sampler No. 2, are graphically compared with mass concentration measurements obtained using the direct electrooptical measuring system and apparatus of the present invention. For example, Aspirated Sampler Nos. 1 and 2 each consisted of a conventional, tubular, filter holder corresponding to the test sampler 18 schematically shown in FIG. 1 and having an inlet end, such as 18a disposed within the interior confines of the aerosol test chamber 10 and having an outlet end 18b connected to a vacuum line, such as 19. With each of the test samplers 18 in position and with the test chamber maintained completely filled with uniform monodisperse liquid aerosol particles generated by the aerosol generator 15, monodisperse particles were aspirated by vacuum line 19 into each of the Samplers at each of various preselected particle diameters ranging from 10 micrometers in particle diameter to about 40 micrometers in particle diameter at measured flow rates of 1 liter per minute or more. The mass concentration for each of the Aspirated Sampler Nos. 1 and 2 was then determined by the conventional gravimetric method of determining the gain in weight of the filter paper contained within the sampler both before and after aerosol sampling. The gravimetrically measured results were then compared against the mass concentration measurements as directly determined by utilization of the system and technique of the present invention. The efficiencies of the Aspirated Samplers 1 and 2 were then mathematically calculated and plotted as the ratios of the mass concentrations collected by each of the Aspirated Samplers at given particle diameters in relation to the helium-neon laser measured mass concentrations. In other words, the plotted % Efficiency of each of the Aspirated Samplers is merely the mass concentration sampled by the Aspirated Samplers divided by the mass concentration as directly measured by the helium-neon laser multiplied by 100%. In FIG. 2 the % Efficiency of each of the Aspirated Samplers is shown for the various monodisperse particle sizes of the aerosol tested. As clearly seen, as the test aerosol particles sizes decrease from a few micrometers or less, the Aspirated Sampler efficiency approaches 100%. However, as the particle sizes progressively increase beyond a few micrometers, the Aspirated Sampler efficiencies rapidly diminish to a % Efficiency of about 10% or less at 40 micrometers.

Thus, it will be appreciated that the present invention permits a determination of aspirated aerosol sampler efficiencies by the quick and convenient expedient of utilizing constant wavelength, high-intensity irradiation for light transmission measurements of monodisperse aerosol particles; provided that the particle sizes are at least about four times larger than the wavelength of the transmitted high-intensity irradiation.

In view of the foregoing, it will be readily appreciated that the apparatus and method of the present invention provide a fast, accurate and highly reliable system and technique for calibration of the accuracy of aerosol samplers in relation to particle sizes being sampled. Moreover, the method and apparatus is not limited to sampler accuracy, or efficiency, measurements, but also can be used wherever it is desirable to continuously monitor in the geometric optical scattering regime the mass concentration of a test aerosol composed of essentially transparent and spherical particles or droplets.

While the present invention has been described in a preferred embodiment is utilizing liquid aerosol particles, or droplets, it has been determined that the system and technique is likewise applicable for electrooptical measurements of solid particles provided that the particles meet the criteria of being essentially transparent and spherical and of a size relative to the constant wavelength of high-intensity irradiation such that optical attenuation is essentially entirely attributable to geometric optical scattering. For example, aerosols composed of microspheres of glass, polystyrene and other similar essentially transparent and spherical solid materials have been successfully utilized to provide reliably accurate mass concentration measurements. Thus, while monodisperse, liquid aerosols ordinarily are preferable for the practice of the present invention by virtue of low material cost considerations and the relative ease of generation of various particle sizes with a liquid aerosol generator, it is to be understood that, in accordance with the broader aspects and innovative features herein described, the invention is not intended to be limited in its broader scope to a system and technique for mass concentration measurements of liquid aerosol only. Moreover, it will also be clearly apparent that other various details of construction, assembly and modes of operation may be modified throughout a wide range of equivalents, and it is, therefore, not the purpose to limit the scope of the present invention otherwise than as necessitated by the breadth of the appended claims.

We claim:

1. An electrooptical system for direct quantitative measurement on a calibrated output meter of the mass concentration per unit volume, in grams/cubic meter, of gaseous aerosols of a liquid substance to be measured, said system comprising:

means defining a transparent glass or plastic chamber within which to confine a gaseous cloud of monodisperse aerosolized droplets, with pinhole side windows for access, without spectral interference;

transmissiometer laser means for projecting a single beam of high-intensity light irradiation of only one selected constant singular wavelength which is not more than one fifth the diameter of a droplet, said beam extending across the interior confines of said chamber, said droplet diameter and said constant wavelength of said high-intensity irradiation selected in relative relationship to each other so as to restrict attenuation of said beam exclusively to attenuation resulting from geometric optical scattering by the interaction of spectral and optical scattering parameters and not attenuation resulting from absorption in these aerosolized monodisperse droplet clouds;

means for generating a fog cloud of uniform liquid droplets of a single constant diameter size, the droplets being transparent and essentially spherical, the aerosol being a gaseous cloud of the unknown substance whose concentration is desired to be measured;

means for filling said chamber with the aerosolized cloud which comprises monodisperse droplets of selected uniform diameter of 5–50 micrometers selected size;

rotary fan means for selective uniform stirring of aerosols while in the chamber, means for pressure equilization so the cloud may not escape through said side windows;

light sensor means interspaced a predetermined distance across said chamber from said irradiation projecting means and disposed in optical alignment with said optical path for sensing and directly measuring the mass concentration of said aerosolized cloud automatically as an instantaneous, ongoing direct and quantitative function of merely sensing and measuring the proportion of said high-intensity irradiation passing through and attenuated by the aerosolized cloud of droplets within said chamber, means for displaying on a calibrated output meter a value for mass concentration, which value is proportional to the natural log of the fractional transmittance of the irradiation, which obeys the relation:

$$C = \frac{D\mu \, \rho}{3 L} \ln\left(\frac{1}{T_\lambda}\right),$$

where C is the aerosol mass concentration (gm/m$^3$), $T_\lambda$ is the fractional transmittance at the subscript $\lambda$ wavelength; $D\mu$ is the effective (mean) diameter of the droplets in $\mu$m; $\rho$ is the particle mass density (gm/cm$^3$); L is the length in meters of the optical path through the aersolized liquid being investigated; and $\lambda$ is the wavelength of irradiation used for observation, in $\mu$m.

2. A system as defined in claim 1, wherein said means for projecting a beam of high-intensity irradiation comprises an irradiation emitter for emitting a beam of high-intensity irradiation of constant wavelength within the spectrum of visible light.

3. A system as defined in claim 1, wherein said irradiation emitter is an emitter for a beam of high-intensity irradiation having a wavelength of 0.63 micrometers.

4. A system as defined in claim 1, wherein said means for generating comprises an aerosol generator having selectively adjustable means providing a capability of accommodating precisely adjustable monodisperse diameter size selectivity over a relatively wide range of discrete aerosol diameter sizes respectively at least four times greater in size than the wavelength of said beam of high-intensity irradiation.

5. A system as defined in claim 4, wherein said adjustable means provides a capability of monodisperse diameter size selectivity for aerosol diameter sizes respectively at least five times greater in size than the wavelength of said beam of high-intensity irradiation.

6. A system as defined in claim 5, wherein said capability of size selectively embraces monodisperse diameter sizes respectively in the range of from about 5 to about 50 micrometers in diameter.

7. A system as defined in claim 4, wherein said aerosol generator provides a capability of generating monodisperse aerosolized droplets in cloud concentrations respectively in the range of 0.1–1.0 gram per cubic meter.

8. A system as defined in claim 7, wherein said aerosol generator is a spinning-disc type of generator for generating aerosolized liquid droplets and having means for selectively adjusting the angular velocity of the spinning disc to provide means for selective adjustment of the diameter size of the aerosolized liquid droplets generated by said generator.

9. A system as defined in claim 1, including means for selectively generating an aerosolized cloud of monodisperse droplets of a selected size diameter.

10. A system as defined in claim 9, wherein said generating means includes means for selectively adjusting the droplet size of the generated monodisperse droplets to a selected monodisperse size diameter coming within a predetermined size range which in relation to the wavelength of said beam of high-intensity irradiation discriminatively restricts attenuation of said beam essentially exclusively to attenuation resulting from geometric optical scattering.

11. A system as defined in claim 9, including means for continuously maintaining said cloud of aerosolized droplets uniformly dispersed throughout the interior confines of said chamber.

12. A system as defined in claim 9, wherein said light sensor means includes indicator means for directly and quantitatively indicating the mass concentration of the aerosolized droplets in said cloud as a function of the magnitude of the attenuated beam of high-intensity irradiation sensed by the light sensor.

* * * * *